(12) United States Patent
Predick (10) Patent No.: US 8,177,814 B2
(45) Date of Patent: May 15, 2012

(54) POSTERIOR SPINAL BRIDGE ASSEMBLY PROVIDING STATIC OR DYNAMIC N-LEVEL SPINAL BRIDGE INTERCONNECTION

(75) Inventor: Daniel Predick, Chicago, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 209 days.

(21) Appl. No.: 12/713,635

(22) Filed: Feb. 26, 2010

(65) Prior Publication Data

US 2010/0217322 A1 Aug. 26, 2010

Related U.S. Application Data

(60) Provisional application No. 61/155,575, filed on Feb. 26, 2009.

(51) Int. Cl.
*A61B 17/70* (2006.01)
(52) U.S. Cl. ........................... 606/250; 606/264
(58) Field of Classification Search .............. 606/247, 606/250, 257, 263, 264, 278, 302, 308
See application file for complete search history.

(56) References Cited

U.S. PATENT DOCUMENTS

| | | | |
|---|---|---|---|
| 4,448,191 A | 5/1984 | Rodnyansky et al. | |
| 5,084,049 A | 1/1992 | Asher et al. | |
| 5,366,455 A | 11/1994 | Dove et al. | |
| 5,470,333 A * | 11/1995 | Ray | 606/261 |
| 5,531,745 A * | 7/1996 | Ray | 606/261 |
| 5,662,652 A | 9/1997 | Schafer et al. | |
| 7,166,111 B2 | 1/2007 | Kolb et al. | |
| 7,473,269 B1 * | 1/2009 | Hynes | 606/279 |
| 7,618,418 B2 * | 11/2009 | Malandain | 606/60 |
| 8,034,078 B2 * | 10/2011 | Laskowitz et al. | 606/246 |
| 2007/0118122 A1 | 5/2007 | Butler et al. | |
| 2008/0306513 A1 | 12/2008 | Winslow et al. | |

* cited by examiner

*Primary Examiner* — Pedro Philogene
(74) *Attorney, Agent, or Firm* — Foley & Lardner LLP (57) ABSTRACT

A bio-compatible posterior spinal bridge assembly provides static or dynamic N-level spinal bridge interconnection between adjacent posterior spinal bridges and posterior spinal bridge assemblies. The posterior spinal bridge assembly includes a spinal bridge that is received in posterior vertebral screw assemblies that are affixed a vertebra and to laterally span the posterior side of the vertebra, and an interconnection element that allows static or dynamic connection between adjacent spinal bridges and/or spinal bridge assemblies. The interconnection element is defined by interconnection members that are carried by the spinal bridge and which provide static or dynamic connection between any number of adjacent spinal bridges/bridge assemblies. The interconnection members are attachable at various positions along the spinal bridge such as medially, laterally, or midline on the spinal bridge. Adjacent spinal bridge assemblies may thus be statically or dynamically linked, connected or coupled to one another via the interconnection members when more than one spinal bridge assembly is used.

13 Claims, 11 Drawing Sheets

POSTERIOR SPINAL BRIDGE ASSEMBLY PROVIDING STATIC OR DYNAMIC N-LEVEL SPINAL BRIDGE INTERCONNECTION

RELATED APPLICATIONS

This U.S. non-provisional patent application claims the benefit of and/or priority to U.S. Provisional Patent Application Ser. No. 61/155,575 filed Feb. 26, 2009, entitled "Posterior Spinal Bridge Assembly Providing Static or Dynamic N-Level Spinal Bridge Interconnection" the entire contents of which is specifically incorporated herein by this reference.

BACKGROUND OF THE INVENTION

1. Field of the Invention

The present invention relates to relates to spinal fixation devices that are attached onto a patient's spine such as spinal rods, spinal rod screws and spinal cross connectors and, more particularly, to posterior spinal bridge or cross assemblies.

2. Background Information

There are many medical situations, because of disease, injury or deformity, where it is necessary to align, hold and/or fix a desired relationship between adjacent vertebral bodies. In order to accomplish this goal, orthopedic spinal surgeons utilize spinal fixation devices, systems and/or assemblies to provide the desired relationship between adjacent vertebral bodies. Such spinal fixation devices typically include one or more spinal fixation elements, such as relatively rigid fixation rods, that are connected to adjacent vertebrae by attaching the rod to anchor devices, systems and/or assemblies affixed onto the vertebrae. The anchor devices are typically spinal bone screw assemblies that include bone screws and screw head/spinal rod connectors.

The spinal fixation rods are typically placed on opposite sides of the spinous processes of adjacent vertebrae in a substantially parallel relationship. Spinal fixation rods may have pre-determined contours according to properties of the target implantation site. Once installed, the spinal fixation rods hold the vertebrae in a desired spatial relationship. It may also be necessary in some circumstances to provide a spinal cross-connector at one or more points between the two spinal fixation rods in order to provide additional stability to the structure. Particularly, adjacent spinal fixation rod assemblies can be made more robust by using a cross-connector to bridge the pair of spinal rods. Current cross-connectors are generally rods themselves that are adapted for connection at ends thereof to the spinal rods.

There are various medical spinal procedures where cross-connectors or current spinal prostheses of any kind do not address all of the issues created by the various medical spinal procedures. One such medical spinal procedure is a spinal decompression procedure. Spinal decompression is achieved in the patient by the removal of several adjacent spinous processes and the elongation and/or stabilization of the adjacent vertebrae through the use of the spinal fixation assemblies such as indicated above (i.e. spinal rods and spinal bone screw/rod holder assemblies). This procedure, however, can contribute to overexposure of the vulnerable spinal cord as well as create the potential for post operative soft tissue cavitation. While current cross-connectors may be used for stabilization of spinal fixation assemblies (and thus the affected vertebrae), they are not always adequate or satisfactory for the intended purpose. Moreover, in some instances, cross connectors are not usable such as when the underlying spinal rod assemblies are not used or are able to be used. In these instances, a spinal bridge assembly may be used. However, current spinal bridge assemblies are not adequate.

Accordingly, there presently exists a need for an improved spinal bridge, spinal bridge assembly, and/or spinal bridge components. Moreover, there presently exists a need for an improved manner of joining adjacent spinal bridges.

SUMMARY OF THE INVENTION

The present invention is a bio-compatible posterior spinal bridge assembly providing static and/or dynamic N-level spinal bridge interconnection between adjacent posterior spinal bridges/posterior spinal bridge assemblies. The present posterior spinal bridge assembly includes a spinal bridge that is configured for reception in posterior vertebral screw assemblies that are affixed posteriorly to a vertebra and to laterally span the posterior side of the vertebra, and an interconnection element that is configured to allow static or dynamic connection between adjacent spinal bridges and/or spinal bridge assemblies.

In one form, the interconnection element is defined by interconnection members that are carried by the spinal bridge and are configured to provide static or dynamic connection between N adjacent spinal bridges/bridge assemblies (i.e. an N-level interconnection).

The static or dynamic interconnection members are attachable at various positions along the spinal bridge. For instance, the interconnection members may be positioned medially, laterally, or midline on the spinal bridge. Adjacent spinal bridge assemblies may thus be statically or dynamically linked, connected or coupled to one another via the interconnection members when more than one spinal bridge assembly is used.

In another form, the interconnection element is defined by a posterior connection plate that is attachable to adjacent spinal bridges and which is configured to allow static or dynamic connection between N adjacent spinal bridges/bridge assemblies (i.e. an N-level interconnection). The connection plate preferably has a lordotic curve and one or more slotted locking pockets for screw placement variability and retention, depending on the level of the connection plate. The caudal most level of the connection plate has a non-slotted pocket for screw mounting. This allows for back-table assembly, ease of placement and increased axial compression support In an embodiment, the posterior connection plate has an a first bore defined therein that is configured to receive and allow coupling to a connector of a first spinal bridge, the first bore providing for static superior/inferior connection to the first spinal bridge while allowing for lateral angulation of the plate relative to the first spinal bridge. The posterior connection plate further has second bore defined therein formed as an oval and configured to receive and allow static or dynamic superior/inferior connection to a second spinal bridge that is adjacent the first spinal bridge.

The bottom of the connection plate may include flats for flush alignment of the connection plate with the various spinal bridges. The flats may be sized and/or configured to provide angulation of the connection plate relative to a mounted spinal bridge.

Further adjacent spinal bridge assemblies may be statically or dynamically linked, connected or coupled to one another via an N-level posterior connection plate when more than one spinal bridge assembly is used. The N-level posterior connection plate has the non-slotted locking caudal pocket as described above with N slotted oval locking pockets that are configured to receive and allow static or dynamic superior/inferior connection to N additional adjacent spinal bridges for each additional level.

The spinal bridge is formed so as to mimic or approximate the removed spinous process to which the spinal bridge is attached, and provides for posterior coverage of exposed spinal cord, soft tissue, Foremen and/or adipose tissue thereof. To this end, the present spinal bridge is formed by first and second legs with a posterior curvature or arch member connecting the first and second legs.

Preferably, but not necessarily, the first and second legs of the spinal bridge each have a generally trapezoidal or pentagonal cross section. This allows for reception in posterior spinal screw assemblies. Each posterior spinal screw assembly has a polyaxial head that is retained on a bone screw and is configured to receive and retain a leg in various orientations.

BRIEF DESCRIPTION OF THE DRAWINGS

The above mentioned and other features, advantages and/or objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non-discussed features may be inherent in component geometry and/or configuration.

DETAILED DESCRIPTION OF EMBODIMENTS OF THE INVENTION

Figure 1:
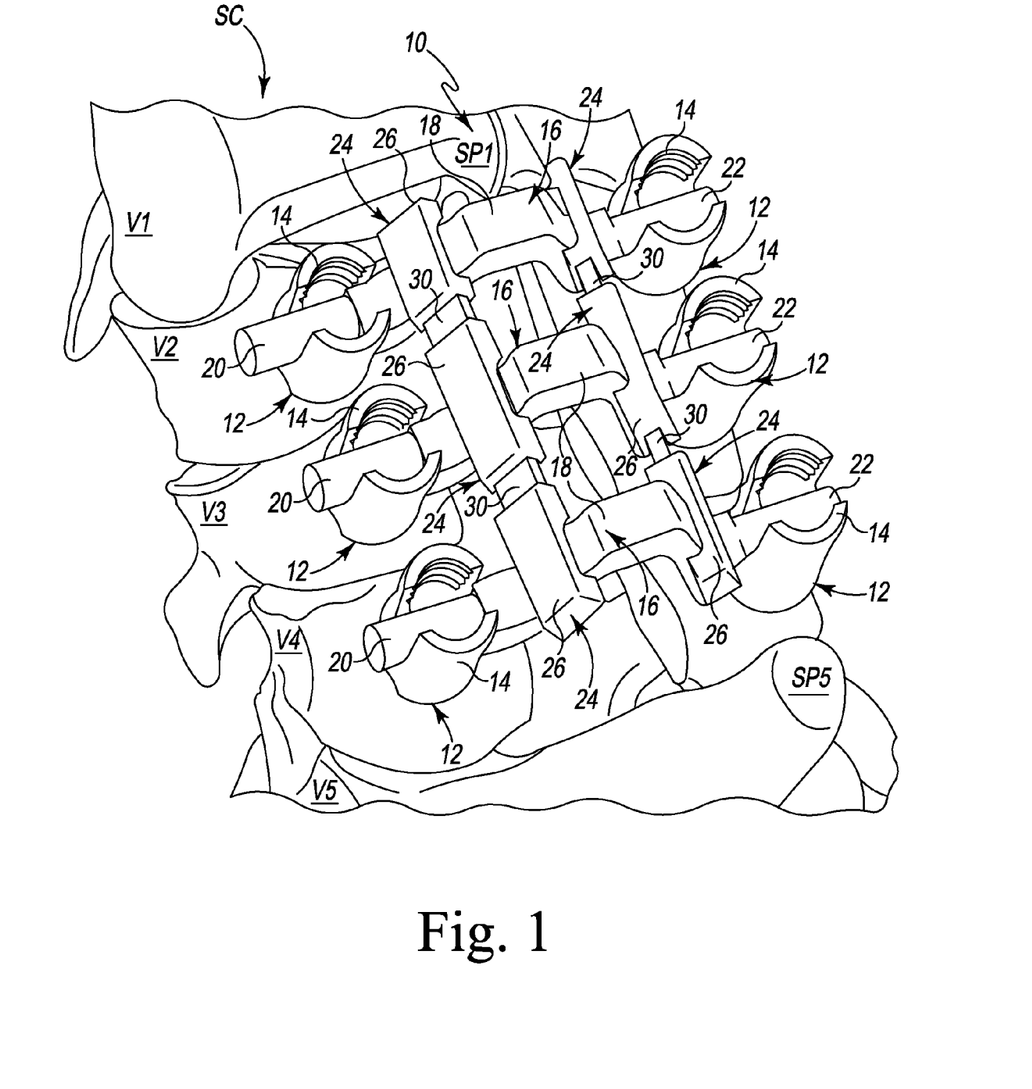
FIG. 1 is a left side posterior perspective view of a section of the cervical portion of a spine having undergone decompression surgery wherein the spinous process has been removed from several of the cervical vertebrae and a 2-level posterior spinal bridge assembly fashioned in accordance with the present principles is mounted thereon, the 3-level posterior spinal bridge assembly having a spinal bridge mounted to and extending between a pair of posterior cervical polyaxial screws that are affixed to a vertebra, the 3-level posterior spinal bridge assembly having medially positioned static/dynamic connection members providing static and/or dynamic interconnection between adjacent posterior spinal bridges.
Figure 2:
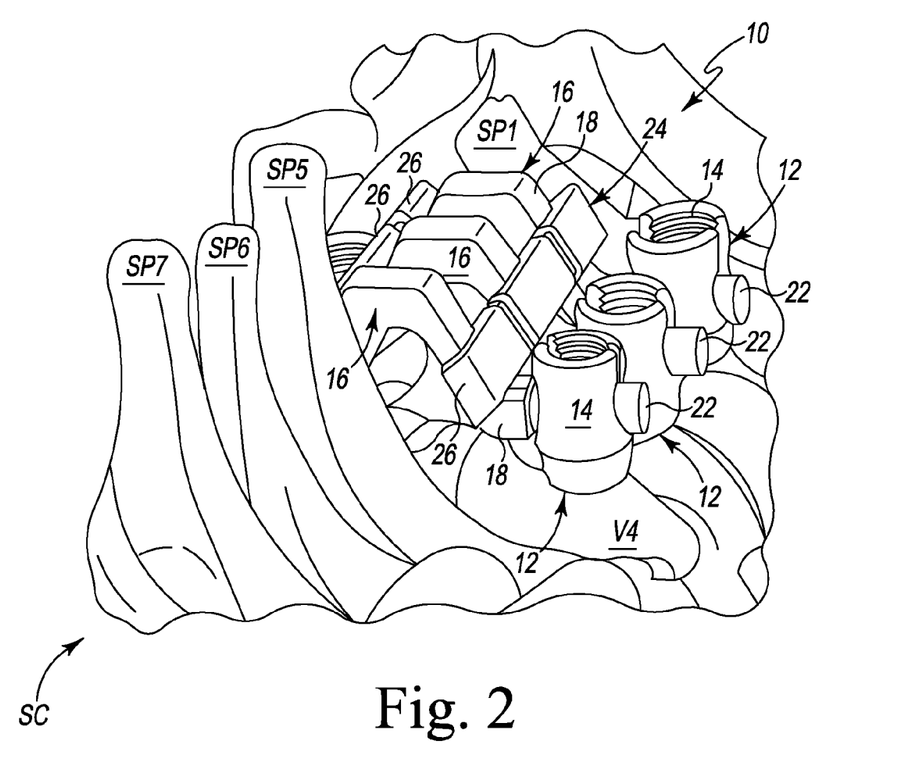
FIG. 2 is a right side posterior perspective view of the cervical portion of the spine of FIG. 1 showing the 2-level posterior bridge assembly with medially positioned static/dynamic interconnection members mounted thereon.
Figure 3:
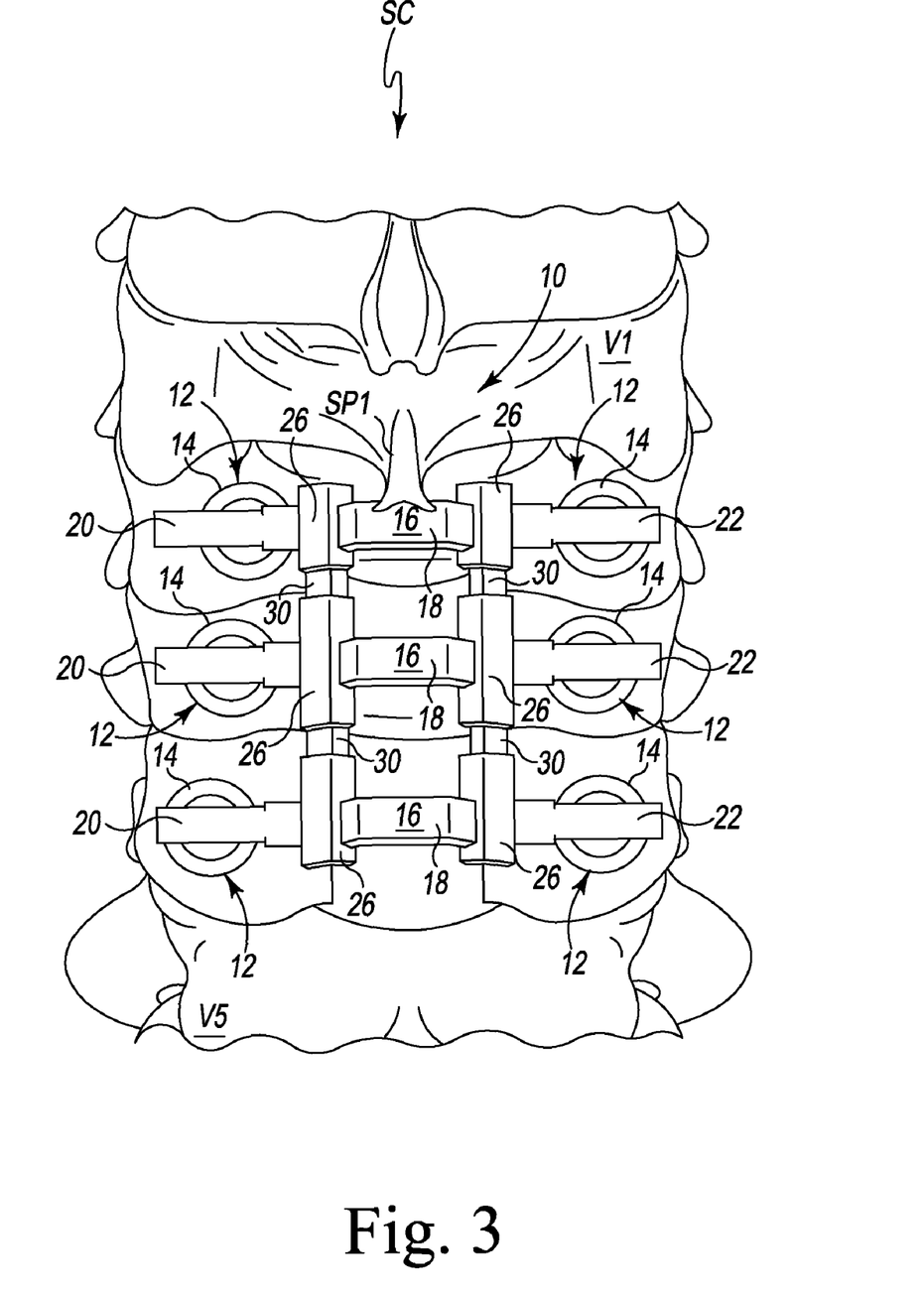
FIG. 3 is a top posterior plan view of the cervical portion of the spine of FIG. 1 again showing the 2-level posterior bridge assembly with medially positioned static/dynamic members mounted thereon.

Referring to FIGS. 1-3, there is depicted various posterior views of a section of a cervical portion of a spine SC having an embodiment of a static and/or dynamic posterior spinal bridge construct in fashioned in accordance with the principles of the present invention. The posterior bridge construct 10 provides static and/or dynamic spinal bridge interconnection between adjacent posterior spinal bridges/spinal bridge assemblies. Particularly, the static/dynamic posterior bridge construct 10 is affixed onto three adjacent vertebrae V2, V3 and V4. The posterior bridge construct 10 is a two level (2-L) posterior bridge assembly as it spans two spinal disc areas bounded by three adjacent vertebrae (V2, V3 and V4), the three adjacent vertebrae V2, V3 and V4 each having a posterior bridge assembly 16 thereon. It should be noted that the vertebrae V2, V3 and V4 have had their spinous process removed. Upper adjacent vertebra V1 (of the shown cervical portion of the spine SC) has its spinous process SP1 intact, while lower adjacent vertebra V5 (of the shown cervical portion of the spine SC) also has its spinous process SP5 intact. It should be appreciated that a posterior bridge construct may consist of a single posterior bridge assembly (i.e. a single level construct) or multiple posterior bridge assemblies (i.e. a multiple level or N-level construct).

Each posterior spinal bridge assembly 16 is made from a biocompatible material such as titanium or stainless steel, however, other biocompatible material, materials or compounds may be used. A posterior spinal bridge assembly consists of a spinal bridge 18 and two static/dynamic interconnection elements 24 that are received on the spinal bridge 18. The spinal bridge 18 consists of an arched, generally rectangular bridge body having a first rod-shaped end 20 and a second rod-shaped end 22. The spinal bridge 18 is arched in the posterior direction to mimic and/or approximate the removed spinous process. The first and second ends 20, 22 are configured for reception in spinal screw assemblies 12 that are affixed to posterior lateral sides of the vertebrae. To this end, the first and second ends 20, 22 preferably have a generally trapezoidal or pentagonal cross-section, but may have other shapes as appropriate. The first and second ends 20, 22 are received in spinal screw heads 14 of the spinal screw assemblies 12. Particularly, the first and second ends 20, 22 are received in complementary configured slots in the head. It should be appreciated that each spinal screw assembly 12 includes a screw (not shown in FIGS. 1-3 but shown as screws 15 in FIGS. 7-13) that are affixed to the vertebrae. The screw 15 provides anchoring to the vertebra and polyaxial attachment to the spinal screw head 14. Moreover, while also not shown in FIGS. 1-3, end caps will be provided that are threadedly received in the spinal rod screw heads 14 in order to retain the bridge ends 20, 22 (but see, e.g., FIG. 11).

Each interconnection element 24 is defined by a generally elongated U-shaped, rectangular connection member 26 that is adapted to be received on the generally rectangular bridge 18. The connection members 26 may be positioned as required on the bridge 18. In FIGS. 1-3, the connection members 26 are medially situated, positioned, placed or oriented on the bridge 18. Moreover, adjacent connection members 26 of adjacent bridge assemblies 16 are connected to each other by connectors 30. The connectors 30 provide static and/or dynamic interconnection of the connection members 26. In the static case, there is little to no inferior/superior movement between adjacent bridge assemblies. In the dynamic case, there is inferior/superior movement between adjacent bridge assemblies. In both cases the interconnection elements 24 and connectors 30 form and/or provide axial (superior/inferior) stabilization of the bridged vertebrae/bridge assemblies 16 while allowing limited axial movement.

Figure 4:
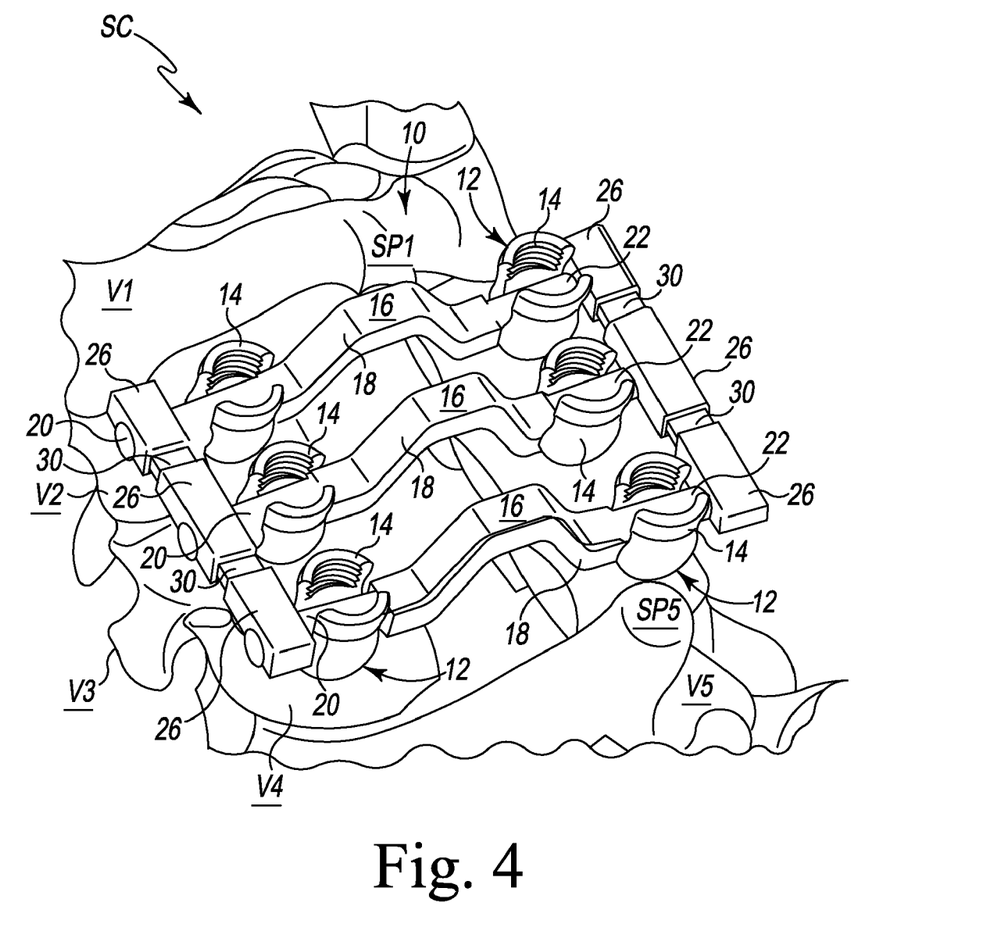
FIG. 4 is a left side posterior perspective view of a section of the cervical portion of a spine having undergone decompression surgery wherein the spinous process has been removed from several of the cervical vertebrae and a 2-level posterior spinal bridge assembly fashioned in accordance with the present principles is mounted thereon, the 2-level posterior spinal bridge assembly having a spinal bridge mounted to and extending between a pair of posterior cervical polyaxial screws that are affixed to a vertebra, the 2-level posterior spinal bridge assembly having laterally positioned static/dynamic connection members providing static and/or dynamic interconnection between adjacent posterior spinal bridges.
Figure 5:
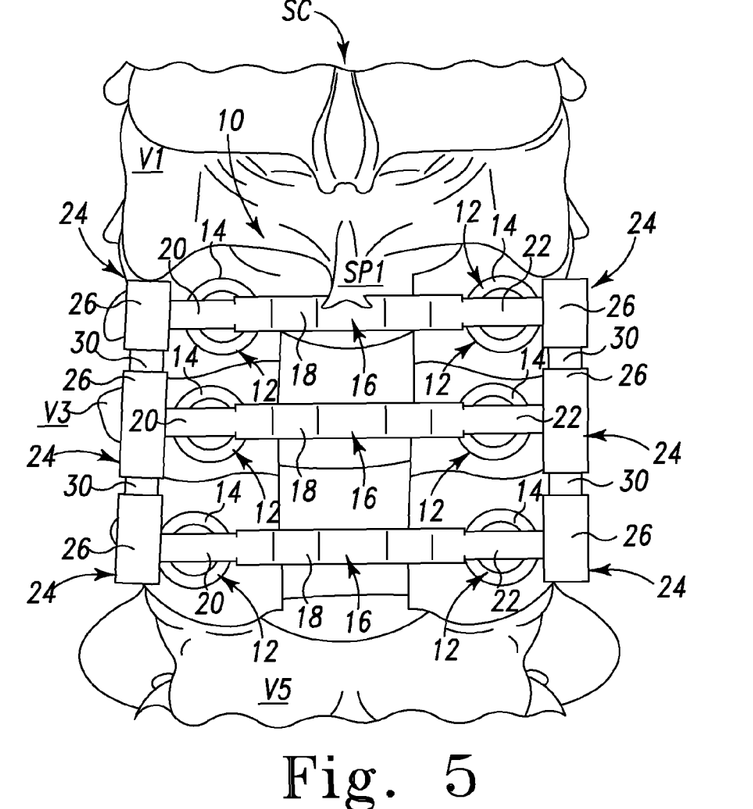
FIG. 5 is a top posterior plan view of the cervical portion of the spine of FIG. 4 showing the 2-level posterior bridge assemblies with laterally positioned static/dynamic members mounted thereon.

Referring to FIGS. 4 and 5, there is depicted two posterior views of the section of the cervical portion of the spine SC having the posterior bridge construct 10 affixed onto the adjacent vertebrae V2, V3 and V4 in like manner to FIGS. 1-3. The posterior bridge construct 10 of FIGS. 4 and 5 thus consists of several posterior bridge assemblies 16. Each posterior bridge assembly 16 again consists of a spinal bridge 18 and one or more interconnection elements 24 that are affixed to the spinal bridge 18. Again, the spinal bridge 18 consists of an arched, generally rectangular bridge body having a first rod-shaped end 20 and a second rod-shaped end 22. The spinal bridge 18 is arched in the posterior direction to mimic and/or approximate the removed spinous process. The first and second ends 20, 22 are configured for reception in the spinal screw assemblies 12 that are affixed to posterior lateral sides of the vertebrae. To this end, the first and second ends 20, 22 preferably have a generally trapezoidal or pentagonal cross-section, but may have other shapes as appropriate. The first and second ends 20, 22 are received in spinal screw heads 14 of the spinal screw assemblies 12. Particularly, the first and second ends 20, 22 are received in complementary configured slots in the head. It should be appreciated that each spinal screw assembly 12 includes a screw (not shown in FIGS. 1-3 but shown as screws 15 in FIGS. 7-13) that is affixed to the vertebrae. The screw 15 provides anchoring to the vertebra and polyaxial attachment to the spinal screw head 14. Moreover, while also not shown in FIGS. 1-3, end caps will be provided that are threadedly received in the spinal rod screw heads 14 in order to retain the bridge ends 20, 22 (but see, e.g., FIG. 11).

Each interconnection element 24 is defined by a generally elongated U-shaped, rectangular connection member 26 that is adapted to be received on the bridge 18. The connection members 26 may be positioned as required on the bridge 18. In FIGS. 4 and 5, the connection members 26 are laterally situated, positioned, placed or oriented on the bridge 18. In this bridge construct, however, the ends 20, 22 of the bridge 18 are elongated such that they extend laterally further (laterally outward) than the ends 20, 22 of the bridge 18 of FIGS. 1-3 in order to receive the connectors 26.

Moreover, adjacent connection members 26 of adjacent bridge assemblies 16 are connected to each other by connectors 30. The connectors 30 provide static and/or dynamic interconnection of the connection members 26. In the static case, there is little to no inferior/superior movement between adjacent bridge assemblies. In the dynamic case, there is inferior/superior movement between adjacent bridge assemblies. In both cases the interconnection elements 24 and connectors 30 form and/or provide axial (superior/inferior) stabilization of the bridged vertebrae/bridge assemblies 16 while allowing for limited axial movement.

Figure 6:
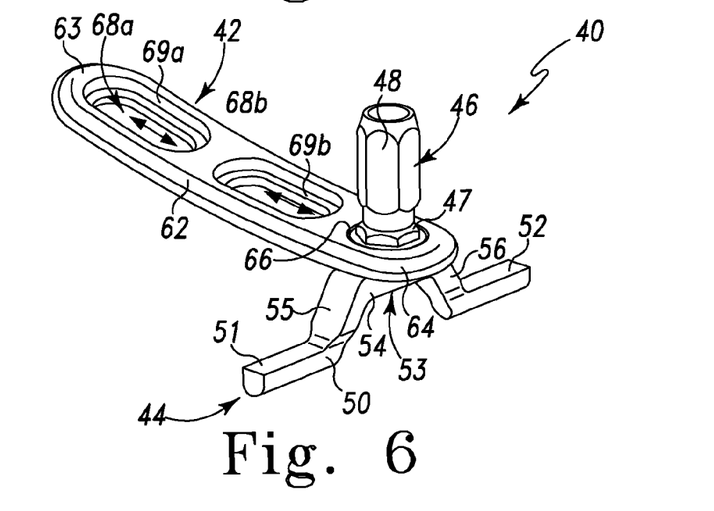
FIG. 6 is an enlarged perspective view of base components of another embodiment of a 2-level posterior spinal bridge assembly, particularly showing a posterior spinal bridge and a 2-level posterior static and/or dynamic connection plate/interconnection element.

Referring now to FIG. 6, base components 40, made from a biocompatible material such as titanium or stainless steel (however, other biocompatible material, materials or compounds may be used) are shown of another embodiment of a static and/or dynamic posterior spinal bridge assembly or construct fashioned in accordance with the present principles. The base components 40 consist of an interconnection element 42 formed as a connection plate 62, and a bridge 44 formed as an arched member 53. The bridge 44 is arched in the posterior direction to mimic and/or approximate the removed spinous process.

The arched member 53 is defined by a generally planar bar 54 with first and second angled portions 55, 56 that slant downwardly from the bar 54 (in the anterior direction). The first angled portion 55 terminates in a first leg 51, while the second angled portion 56 terminates in a second leg 52. A clearance distance or height (see "h" in FIG. 13) is thus created between the connection bar 54 and the first and second legs 51, 52. The first and second legs 51, 52 have a generally trapezoidal or pentagonal cross section for reception in the spinal screw assemblies 12 that are affixed to posterior lateral sides of the vertebrae as shown in Figures. Thus the first and second ends 51, 52 are received in spinal screw heads 14 of the spinal screw assemblies 12. Particularly, the first and second ends 20, 22 are received in complementary configured slots in the head 14 of the screw assembly 12.

Figure 7:
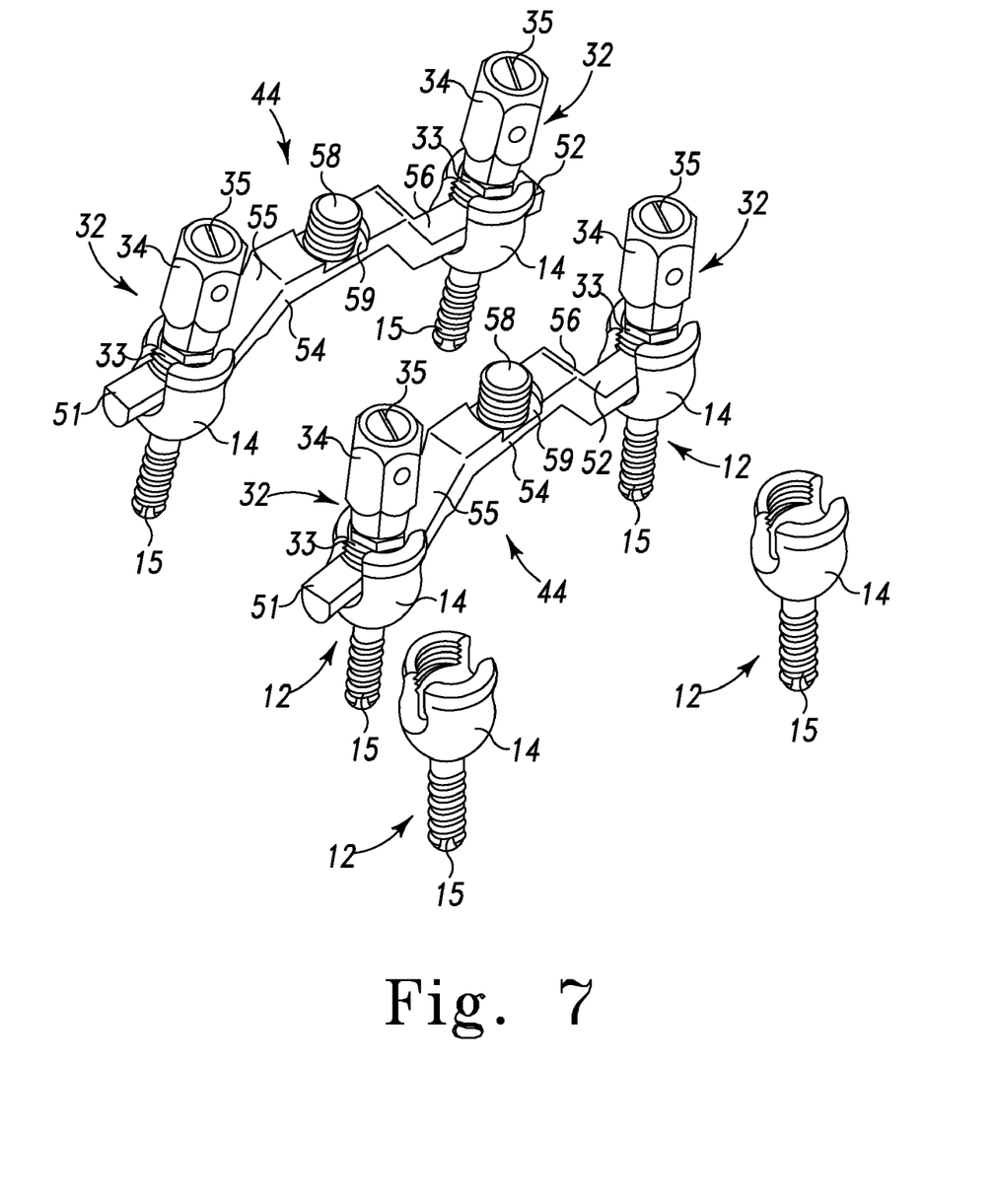
FIG. 7 illustrates steps in the installation of the 2-level posterior spinal bridge assembly of FIG. 6.

As best seen in FIG. 7, a connector 58 is provided on the upper (posterior) side of the bar 54. While the connector 58 may take various forms, the connector 58 is shown embodied as a threaded rod, post or shaft extending from a cutout area 59 on the upper side of the bar 54. The threaded shaft allows reception of a threaded nut or the like. The connector 58 facilitates connection of the plate 62 to the bridge 44.

Figure 11:
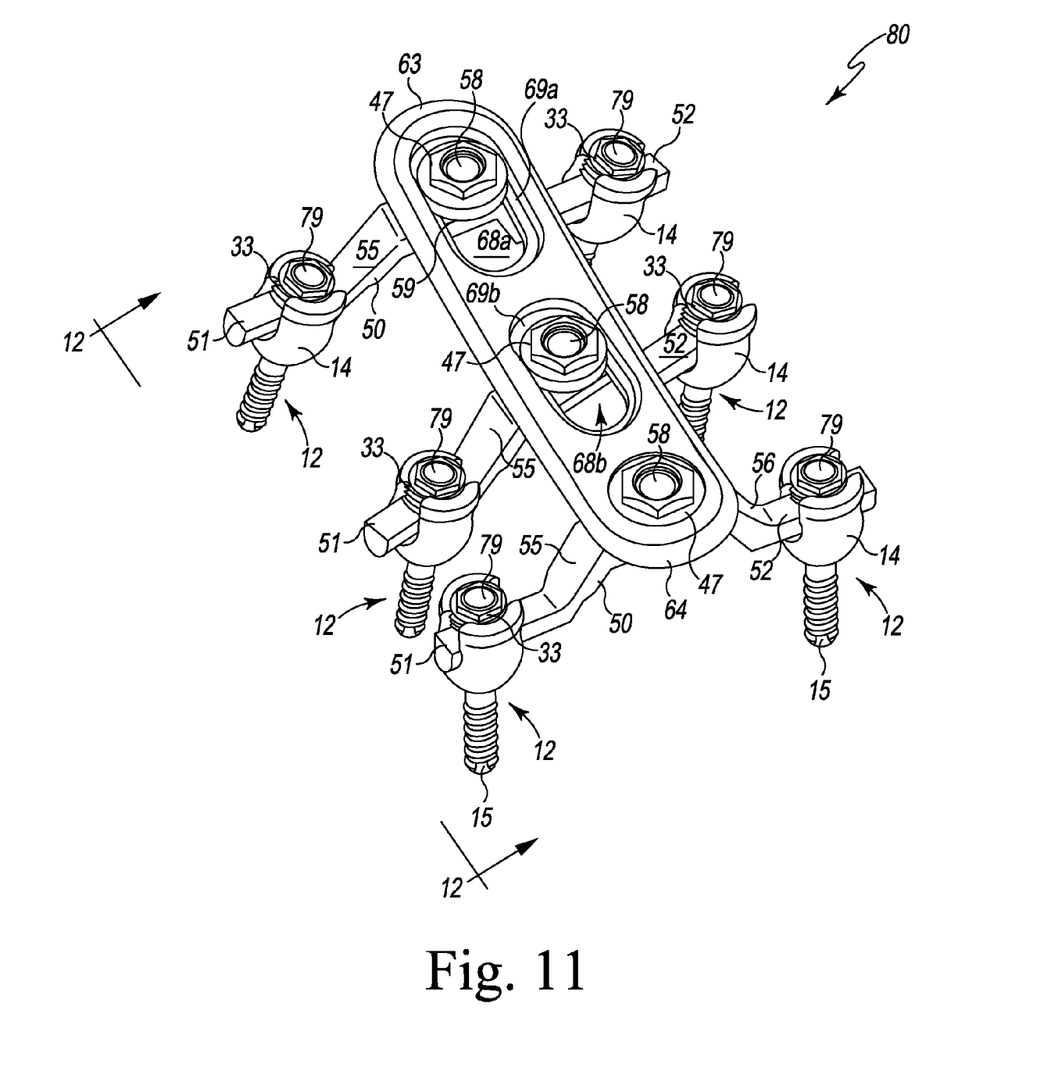
FIG. 11 depicts the installed 2-level posterior spinal bridge assembly of FIGS. 6-10.
Figure 12:
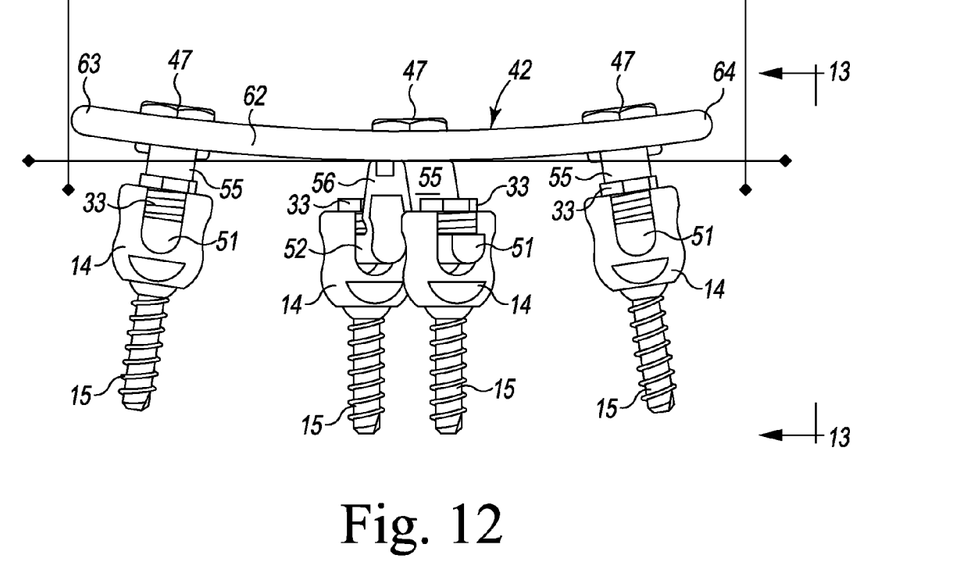
FIG. 12 is a side (lateral) plan view of the 2-level posterior spinal bridge assembly of FIG. 11 taken along line 12-12 thereof.

The connection plate 62 is formed in a generally elongated oval shape (see, e.g. FIGS. 8-11) defining a first end 63 and a second end 64 with the plate 62 having a slight posterior curvature (see, e.g. FIG. 12). A first bore or hole 66 is provided at the second end 64 of the connection plate 63. The first bore 66 is situated at the caudal end 64 of the plate 62 and includes an inner rim or ledge (not seen—but for like structures, e.g., rims/ledges 69a, 69b of pockets 68a, 68b as best seen in FIGS. 6, 8-9 and 11) which together define a first locking pocket. The first bore 66 is generally circular to provide static or fixed positional anchoring of the plate 63 to the bridge 44 while allowing pivoting thereof relative to the bridge 44 (which may be referred to as an anchoring pocket).

The structure of the first locking pocket 66 provides for fixation of the caudal end 64 of the plate 62 to a caudally-positioned bridge 44.

Figure 13:
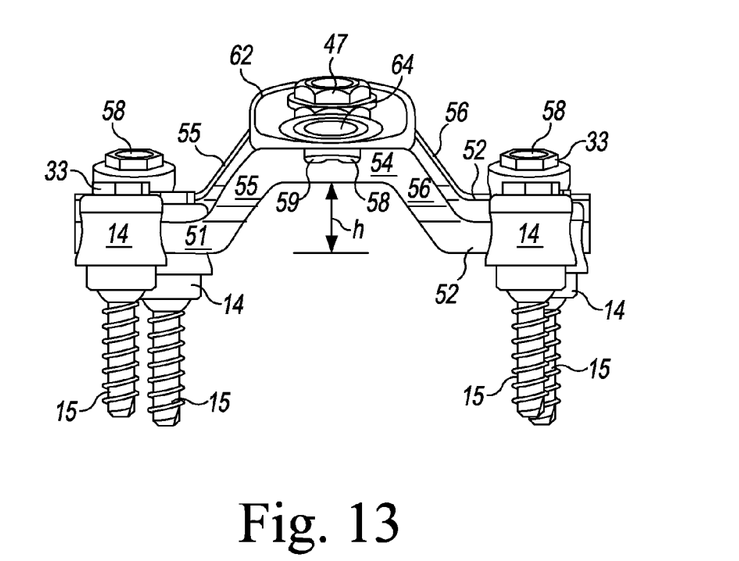
FIG. 13 is a front (caudal end) plan view of the 2-level posterior spinal bridge assembly of FIG. 12 taken along line 13-13 thereof.

As shown in FIGS. 11-13, a locking nut 47 is received in the first locking pocket 66 and onto the threaded shaft 58 for locking fixation of the end 64 of the plate 62. As shown in FIG. 6 and others (e.g. FIGS. 8 and 9), the locking nut 47 is installed onto the threaded shaft 58 and received in the first pocket 66 of the plate 62 initially as a portion of a fixation assembly 46. The fixation assembly 46 includes an elongated driver nut 48 attached to the locking nut 47. The driver nut 48 is received by a driving tool (not shown) and allows placement of the locking nut 47 into a pocket of the plate and onto the threaded shaft of the bridge. The driver nut 48 is snapped off from the locking nut 47 once the locking nut is properly fixed to the plate/bridge. The fixation assembly 46 provides the manner in which the plate is fixed to the bridges 44, e.g. the locking nuts 47 as received on the threaded shaft of a bridge and a pocket of the plate.

The connection plate 62 has a second bore or hole 68a provided at the first end 63 thereof that is generally elongated or oval in shape so as to define a slot. The second bore 68a is situated at the cephal end 63 of the plate 62 and includes an inner rim or ledge 69a (see, e.g., FIGS. 6, 8-9 and 11) which together define a second locking pocket (or a first slotted locking pocket). The second locking pocket provides for inferior/superior (cephal/caudal) adjustability or dynamic positional anchoring of the plate 63 to a cephally-positioned bridge 44 (as represented by the double-headed arrow within the bore 68a). Moreover, the structure of the second locking pocket provides for fixing the cephal end 63 of the plate 62 to the cephally-positioned bridge 44.

The connection plate 62 has a third bore or hole 68b provided between the first and second bores 66, 68a that is generally elongated or oval in shape so as to define a slot. The third bore 68b is situated medially of the cephal end 63 and caudal end 64 of the plate 62 and includes an inner rim or ledge 69b (see, e.g., FIGS. 6, 8-9 and 11) which together define a third locking pocket (or a second slotted locking pocket). The third locking pocket provides for inferior/superior (cephal/caudal) adjustability or dynamic positional anchoring of the plate 63 to a medially-positioned bridge 44 (as represented by the double-headed arrow within the bore 68b). Moreover, the structure of the second locking pocket provides for fixing the medial portion of the plate 62 to the medially-positioned bridge 44.

Figure 10:
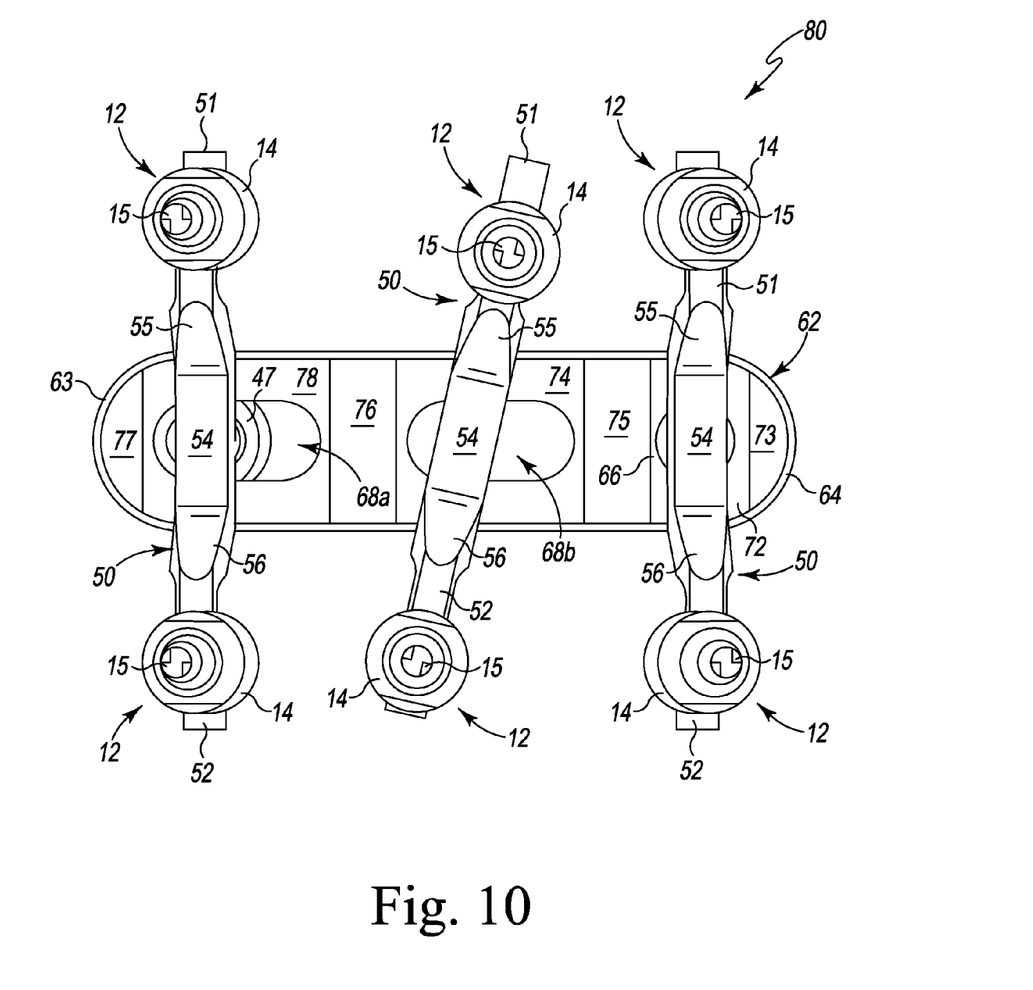
FIG. 10 is a bottom (anterior) plan view of the 2-level posterior spinal bridge assembly of FIG. 9 taken along line 10-10 thereof.

Referring to FIG. 10, the underside or anterior side of the connection plate 62 is shown. Adjacent and about the first pocket 66, the connection plate 62 has a flat 72 defined between caudal end boss 73 and medial-caudal boss 75. The flat 72 provides an area to accommodate various angular orientations of the bar 54 of the caudal-most support body 50. Adjacent and about the first slotted pocket 68a, the connection plate 62 has an elongated flat 78 defined between cephal end boss 77 and medial-cephal boss 76. The flat 78 provides an area to accommodate various angular orientations of the bar 54 of the cephal-most support body 50 as well as longitudinal positions along the slot 68a. Adjacent and about the second slotted pocket 68b, the connection plate 62 has a flat 74 defined between the medial-cephal boss 76 and the medial-caudal boss 75. The flat 74 provides an area to accommodate various angular orientations of the bar 54 of the medial support body 50 as well as longitudinal positions along the slot 68b.

It should be appreciated that the plate 63 is a 2-level (2-L) plate and thus has two (2) slotted (static or dynamic) locking pockets 68a and 68b and a single (1) static locking pocket 66. If the plate 63 was a one level (1-L) plate, there would be only a single (1) slotted locking pocket 68a and a single (1) static locking pocket 66. A three level (3-L) plate (not shown) would have three (3) slotted locking pockets 68a, 68b, 68c and a single (1) static locking pocket 66. Therefore, multiple level (N-level) plates therefore have N slotted locking pockets 68a . . . N and a single static locking pocket 66.

It should be appreciated that the various components of the present spinal bridge assembly may be made in different sizes and/or dimensions as appropriate. For instance, the posterior connection plate may be made in various thicknesses for various applications and/or anatomies. A connection plate thickness of approximately 3 mm is contemplated; other thicknesses, however, may be made. Similarly, the bridge or cross member support may be made with different clearance heights and/or spanning widths as well as thickness. A bridge or cross member support clearance height of approximately 7 mm above the rod axis of the polyaxially screw head is contemplated; other clearance heights, however, may be made. A spanning width of approximately 50 mm, allowing for 10 mm of run-on-rod for locking variability is also contemplated for the bridge; other spanning widths, however, may be made.

With particular reference to FIGS. 7-13, a possible manner of installation of the posterior spinal bridge assembly 80 will be described. FIGS. 7-13 show various stages of assembly (installation) of the components for the present posterior spinal bridge assembly. For clarity, the vertebrae to which the posterior spinal bridge assembly 80 is being mounted are not shown, it being understood that the vertebrae and mounting of the screw assemblies would be the same as shown in FIGS. 1-5. As illustrated in FIG. 7, a first step is to install the vertebral screw assemblies 12 onto the vertebrae. This may be accomplished using standard vertebral bone screw assembly procedures. The spanning width between the polyaxial screw assemblies 12 is measured and a proper bridge (cross member support) size is determined. The appropriate bridge is then inserted into the polyaxial screw heads 12 and breakaway screw head nut assemblies 32 are positioned therein. At this time, placement of the caudal-most bridge is excluded.

A breakaway screw head nut assembly 32 includes an elongated driver nut 34 attached to a screw head locking nut 33. The driver nut 34 is received by a driving tool (not shown) and allows placement of the locking nut 33 into the threaded end of a screw head 14 of the screw assembly 12. A set screw 35 situated in the driver nut 34 has a set screw portion 79 that is threadedly received in the locking nut 33 and fixes against the respective ends 51, 52 when threadedly tighten into the locking nut 33 (see FIG. 11 for an installed locking nut 33 and the set screw portion 79 of the set screw 35). The driver nut 34 is snapped off from the locking nut 33 once the locking nut is properly fixed to the screw head 14. The fixation assembly 32 provides the manner in which the bridge 44 is fixed to the screw assemblies 12.

Figure 8:
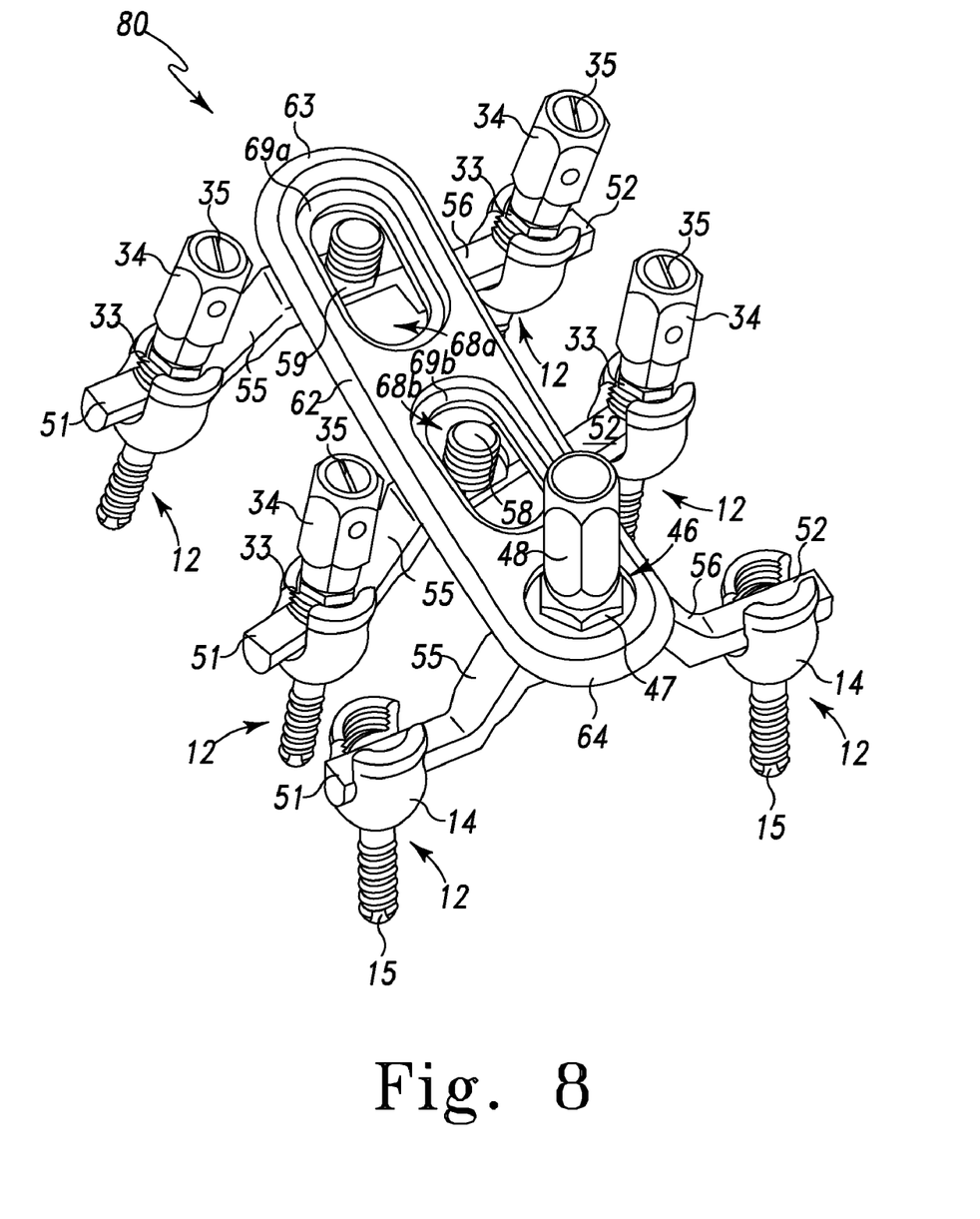
FIG. 8 illustrates next steps in the installation of the 2-level posterior spinal bridge assembly of FIG. 7.
Figure 9:
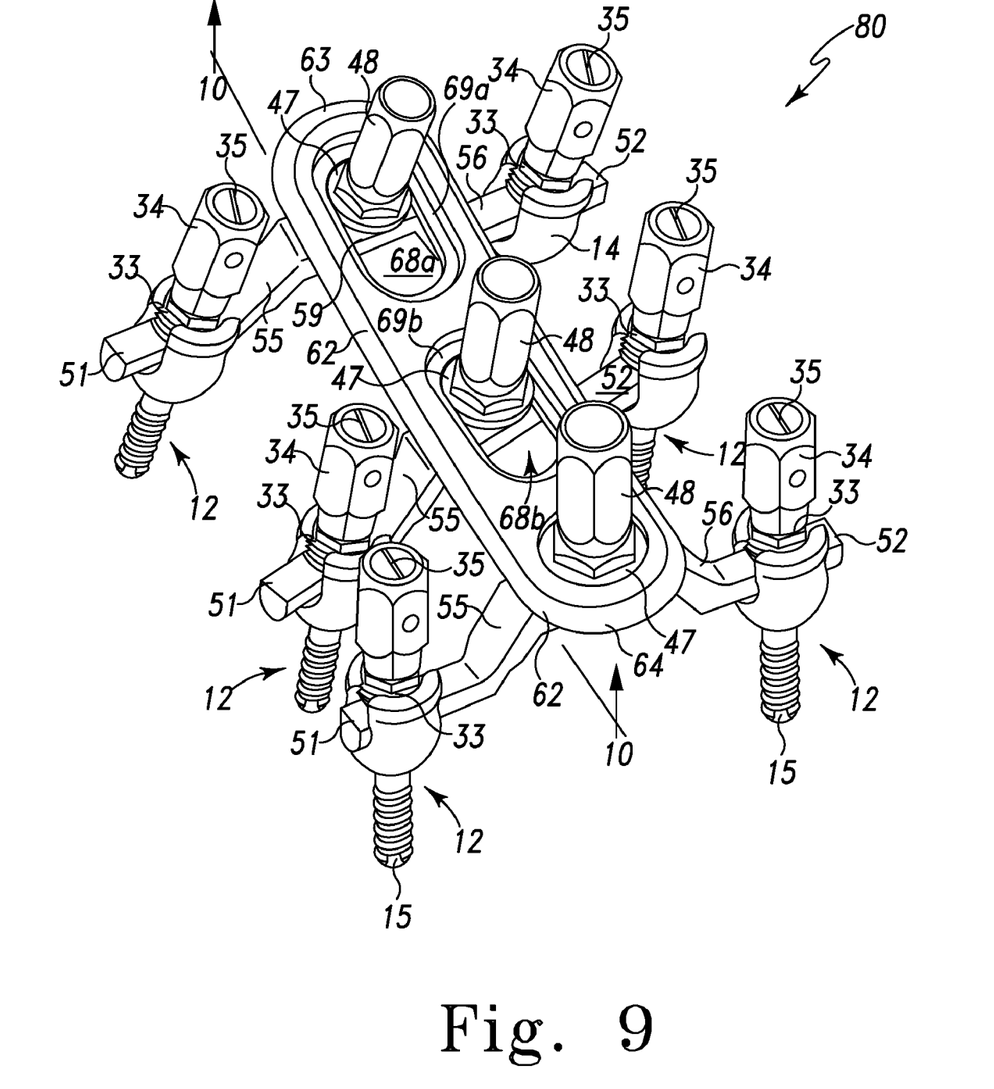
FIG. 9 illustrates further steps in the installation of the 2-level posterior spinal bridge assembly of FIG. 8.

Next, appropriate fixation points are measured using a plate template for selection of an appropriate plate size. The plate is then bent as necessary. As shown in FIG. 8, the appropriate plate 62 is then situated on the supports 44 (backtable) with placement then hand tightening of the breakaway fixation assembly 46 on the caudal non-slotted pocket 66. Thereafter, as shown in FIG. 9, breakaway fixation assemblies 46 are placed then hand-tightened onto the slotted locking pockets 68a, 68b of the plate 62. Appropriate angulation of the plate is achieved. As shown in FIG. 11, all nuts have been tightened and the breakaway assemblies have been removed.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A posterior spinal bridge assembly for attachment to a spine having a first vertebrae and a second vertebrae, the posterior spinal bridge assembly comprising:
   a first posterior spinal bridge element having first and second co-axial arms received in respective first and second posterior vertebral screw assemblies that are affixed posteriorly to opposite sides of the first vertebrae, and an arched section disposed between the first and second co-axial arms, the arched section extending posterior to the first vertebrae when the first posterior spinal bridge element is received in the first and second posterior vertebral screw assemblies and having a first threaded shaft extending therefrom;
   a second posterior spinal bridge element having first and second co-axial arms received in respective first and second posterior vertebral screw assemblies that are affixed posteriorly to opposite sides of the second vertebrae, and an arched section disposed between the first and second co-axial arms, the arched section extending posterior to the second vertebrae when the second posterior spinal bridge element is received in the first and second posterior vertebral screw assemblies and having a second threaded shaft extending therefrom; and
   an interconnection element connectable to the first and second posterior spinal bridge elements and allowing dynamic interconnection between adjacent posterior spinal bridge elements, the interconnection element comprising:
      a caudel end having a circular bore with an inner rim to define a first locking pocket;
      a cephal end having a first elongated bore with an inner rim to define a second locking pocket, wherein the second locking pocket provides dynamic positional anchoring;
      a first locking nut received in the first locking pocket and onto the first threaded shaft extending from the first posterior spinal bridge element;
      a second locking nut received in the second locking pocket and onto the second threaded shaft extending from the second posterior spinal bridge element.

2. The posterior spinal bridge assembly of claim 1, wherein the arched portion of each posterior spinal bridge element has a rectangular cross section.

3. The posterior spinal bridge assembly of claim 1, wherein the interconnection element comprises a plate configured for connection to the arched section of each posterior spinal bridge element.

4. The posterior spinal bridge assembly of claim 3, wherein:
   each one of the plurality of posterior spinal bridge assemblies includes a mount on its arched section; and
   the plate includes a second elongated bore located between the circular bore and the first elongated bore, the second elongated bore positioned to be dynamically received onto a separate mount of a third posterior spinal bridge element located between the first and second posterior spinal bridge elements.

5. The posterior spinal bridge assembly of claim 4, wherein an underside of the plate comprises a first flat area that contacts the upper side of the of the arched section of the first spinal bridge element, and a second flat area that contacts an upper side of the arched section of the second spinal bridge element.

6. The posterior spinal bridge assembly of claim 5, wherein the plate has a lordotic curvature.

7. The posterior spinal bridge assembly of claim 1, wherein the first locking pocket provides fixed positional anchoring of the interconnection element relative to a longitudinal axis of the interconnection element.

8. A posterior spinal bridge assembly for attachment to a spine having a first vertebrae and a second vertebrae, the posterior spinal bridge assembly comprising:
   a first spinal bridge element to laterally span the posterior side of a vertebra, each spinal bridge element having first and second co-axial arms received in respective first and second posterior vertebral screw assemblies that are affixed posteriorly to opposite sides of the first vertebrae, and an arched section disposed between the first and second co-axial arms, the arched section extending posterior to the vertebrae when the first spinal bridge element is received in the first and second posterior vertebral screw assemblies;
   a second spinal bridge element to laterally span the posterior side of a vertebra, the second spinal bridge element having first and second co-axial arms received in respective first and second posterior vertebral screw assemblies that are affixed posteriorly to opposite sides of second vertebrae, and an arched section disposed between the first and second co-axial arms, the arched section extending posterior to the vertebrae when the second spinal bridge element is received in the first and second posterior vertebral screw assemblies; and
   an interconnection element connectable to the first and second posterior spinal bridge elements, the interconnection element comprising:
      a caudel end having a circular bore defining a first locking pocket, wherein the first locking pocket provides pivoting movement of the interconnection element relative to the first spinal bridge element about the axis of the circular bore and provides fixed positional anchoring of the interconnection element relative to a longitudinal axis of the interconnection element;
      a cephal end having a first elongated bore defining a second locking pocket, wherein the second locking pocket provides dynamic positional anchoring.

9. The posterior spinal bridge assembly of claim 8, wherein the arched portion of each spinal bridge element has a rectangular cross section.

10. The posterior spinal bridge assembly of claim 8, wherein the interconnection element comprises a plate configured for connection to the arched section of each spinal bridge element.

11. The posterior spinal bridge assembly of claim 10, wherein:
   each one of the plurality of spinal bridge assemblies includes a mount on its arched section; and
   the plate includes a second elongated bore located between the circular bore and the first elongated bore, the second elongated bore positioned to be dynamically received onto a separate mount of a third spinal bridge element located between the first and second posterior spinal bridge elements.

12. The posterior spinal bridge assembly of claim 11, wherein an underside of the plate comprises a first flat area that contacts the upper side of the of the arched section of the first spinal bridge element, and a second flat area that contacts an upper side of the arched section of the second spinal bridge element.

13. The posterior spinal bridge assembly of claim 12, wherein the plate has a lordotic curvature.

* * * * *